United States Patent

Agouridas et al.

Patent Number: 5,543,400
Date of Patent: Aug. 6, 1996

[54] ERYTHROMYCIN COMPOUNDS

[75] Inventors: Constantin Agouridas, Nogent sur Marne; Alain Bonnefoy, Les Lilas; Jean-François Chantot, Gressy en France; Alexis Denis; Odile Le Martret, both of Paris, all of France

[73] Assignee: Roussel Uclaf, France

[21] Appl. No.: 146,695

[22] Filed: Nov. 1, 1993

[30] Foreign Application Priority Data

Nov. 5, 1992 [FR] France ................... 92 13321

[51] Int. Cl.⁶ .................. A61K 31/70; C07H 17/08
[52] U.S. Cl. .................. 514/29; 536/7.2; 536/7.3; 536/7.4
[58] Field of Search .................. 536/7.2, 7.5, 7.3; 514/29

[56] References Cited

U.S. PATENT DOCUMENTS 4,920,102  4/1990  Gidda et al. .................. 514/28
5,175,150  12/1992  Omura et al. .................. 514/29

OTHER PUBLICATIONS

Tetrahedron vol. 37 Supplement No. 1, pp. 165–173 (1981) "Stereochemistry of Macrolides".

*Primary Examiner*—Elli Peselev
*Attorney, Agent, or Firm*—Bierman & Muserlian

[57] ABSTRACT

A compound selected from the group consisting of a compound of the formula

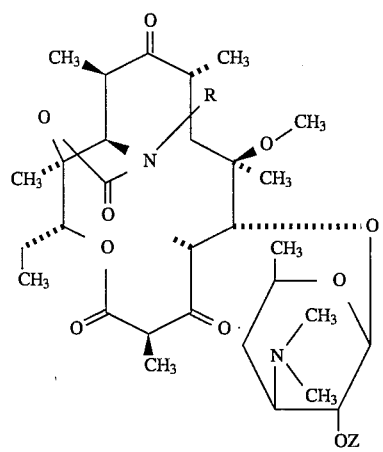

wherein R is

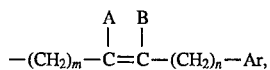

m and n are individually integers from 0 to 6, A and B are individually a member selected from the group consisting of hydrogen, halogen and alkyl of 1 to 8 carbon atoms, the double bond geometry being E or Z or E+Z or A and B form a third bond between the carbon atoms to which they are attached, Ar is selected from the group consisting of a) carbocyclic aryl of up to 18 carbon atoms optionally substituted with at least one member of the group consisting of free carboxy, alkoxycarbonyl, carboxy salified with a non-toxic, pharmaceutically acceptable base, amidified carboxy, —OH, halogen, —$NO_2$, —CN, alkyl, alkenyl, alkynyl, alkoxy, alkenyloxy, alkynyloxy, alkylthio, alkenylthio and alkynylthio of up to 12 carbon atoms, N-alkyl, N-alkenyl and N-alkynyl of up to 12 carbon atoms and cycloalkyl of 3 to 12 carbon atoms, all optionally substituted with at least one halogen and

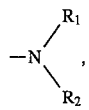

$R_1$ and $R_2$ are individually selected from the group consisting of hydrogen, alkyl of 1 to 12 carbon atoms, carbocyclic aryl, aryloxy, arylthio, heterocyclic aryl and aryloxy and arylthio containing at least one heteroatom, all optionally substituted as above and b) heterocyclic aryl having at least one heteroatom optionally substituted with at least one of the above substituents, Z is hydrogen or acyl of an organic carboxylic acid of 1 to 18 carbon atoms and their non-toxic, pharmaceutically acceptable acid addition salts having antibiotic properties.

22 Claims, No Drawings

ERYTHROMYCIN COMPOUNDS

OBJECTS OF THE INVENTION

It is an object of the invention to provide the novel compounds of formula I and their non-toxic, pharmaceutically acceptable acid addition salts and a process for their preparation.

It is another object of the invention to provide novel antibiotic compositions and a method of combatting bacterial infections.

These and other objects and advantages of the invention will become obvious from the following detailed description.

THE INVENTION

The novel compounds of the invention are selected from the group consisting of a compound of the formula

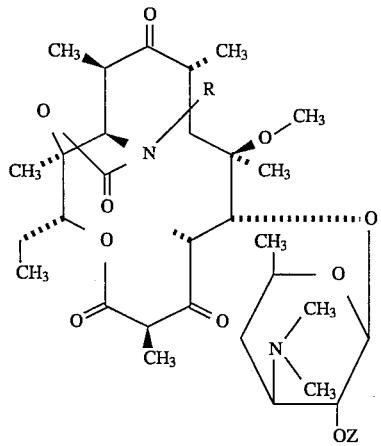

wherein R is

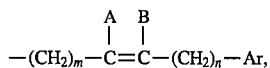

m and n are individually integers from 0 to 6, A and B are individually a member selected from the group consisting of hydrogen, halogen and alkyl of 1 to 8 carbon atoms, the double bond geometry being E or Z or E+Z or A and B for a third bond between the carbon atoms to which they are attached, Ar is selected from the group consisting of a) carbocyclic aryl of up to 18 carbon atoms optionally substituted with at least one member of the group consisting of free carboxy, alkoxycarbonyl, carboxy salified with a non-toxic, pharmaceutically acceptable base, amidified carboxy,, —OH, halogen, —NO$_2$, —CN, alkyl, alkenyl, alkynyl, alkoxy, alkenyloxy, alkynyloxy, alkylthio, alkenylthio and alkynylthio of up to 12 carbon atoms, N-alkyl, N-alkenyl and N-alkynyl of up to 12 carbon atoms and cycloalkyl of 3 to 12 carbon atoms, all optionally substituted with at least one halogen and

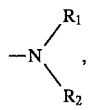

R$_1$ and R$_2$ are individually selected from the group consisting of hydrogen, alkyl of 1 to 12 carbon atoms, carbocyclic aryl, aryloxy, arylthio, heterocyclic aryl and aryloxy and arylthio containing at least one heteroatom, all optionally substituted as above and b) heterocyclic aryl having at least one heteroatom optionally substituted with at least one of the above substituents, Z is hydrogen or acyl of an organic carboxylic acid of 1 to 18 carbon atoms and their non-toxic, pharmaceutically acceptable acid addition salts.

Ar, when it is carbocyclic aryl, is preferably phenyl or naphthyl and when it is heterocyclic aryl, is preferably monocyclic heteroaryl of 5 to 6 ring members containing one or more heteroatoms or a condensed polycyclic system with each ring having 5 or 6 ring members and optionally one or more heteroatoms selected from —O—, —S— and nitrogen.

Examples of the monocyclic heteroaryl radical with 5 members are thienyl, furyl, pyrrolyl, thiazolyl, pyridyl, pyrimidinyl, pyridazinyl and pyrazinyl and examples of the condensed polycyclic heteroaryl are indolyl, benzofuryl, benzothienyl or quinolinyl or the remainder of a purine base such as adenine.

Examples of alkyl, alkenyl or alkynyl are methyl, ethyl, propyl, isopropyl, n-butyl, isobutyl, terbutyl, decyl or dodecyl, vinyl, allyl, ethynyl, propynyl, propargyl, cyclobutyl, cyclopentyl and cyclohexyl. Halogen is preferably fluorine, chlorine or bromine and alkyl substituted by halogen is preferably —CHCl$_2$. —CHBr$_2$, —CHF$_2$, —CCl$_3$, —CBr$_3$, —CF$_3$, —CH$_2$CF$_3$, —CH$_2$CH$_2$CCl$_3$ or —CH$_2$CH$_2$CF$_3$. The carboxylic acid remainder is preferably acetyl, propionyl, butyryl, isobutyryl, n-valeryl, isovaleryl, tert-valeryl and pivalyl.

Among the preferred compounds of the formula I are those wherein Z is hydrogen, those wherein A and B are hydrogen or form a third bond between the carbons to which they are attached, those wherein m is 1 or 2, those wherein n is 0 or 1, those wherein Ar is carbocyclic aryl optionally substituted such as phenyl optionally substituted with fluorine, —CF$_3$ or phenyl and most preferably Ar is phenyl.

The novel process of the invention for the preparation of a compound of formula I comprises reacting a compound of the formula

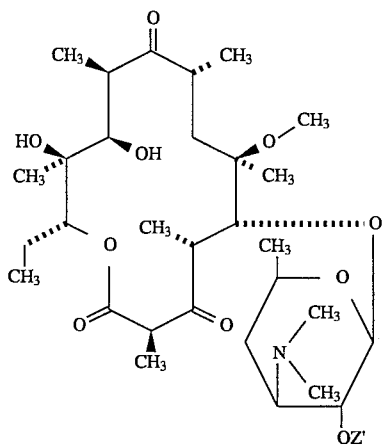

wherein Z' is acyl of an organic carboxylic acid of up to 18 carbon atoms with an agent to selectively activate the 11-hydroxyl to obtain a compound of the formula

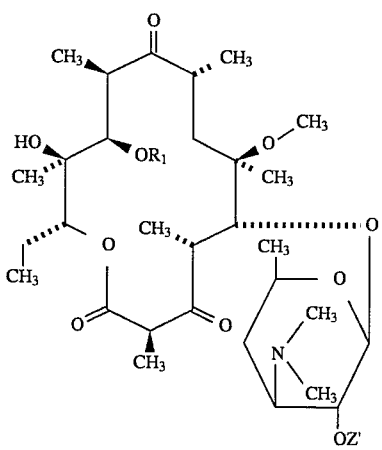

wherein $R_1$ is the remainder of the activator group, subjecting the latter to the action of a base to obtain a compound of the formula

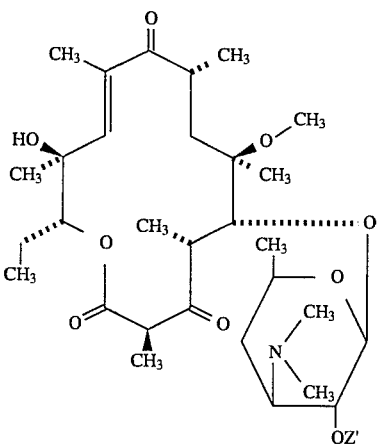

subjecting the latter either to the action of a compound of the formula $$R-N=C=O \quad V$$

wherein R has the above meaning to obtain a compound of the formula

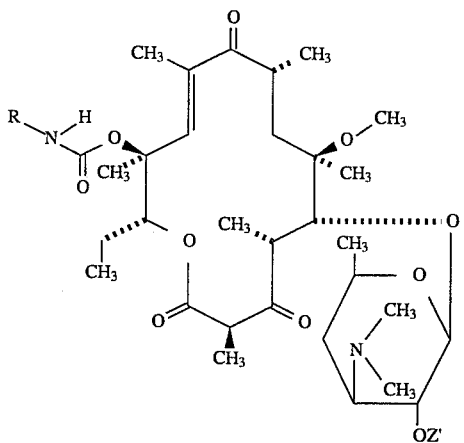

which is cyclized either spontaneously by heating, or which is subjected to the action of a cyclization agent to obtain a compound of the formula

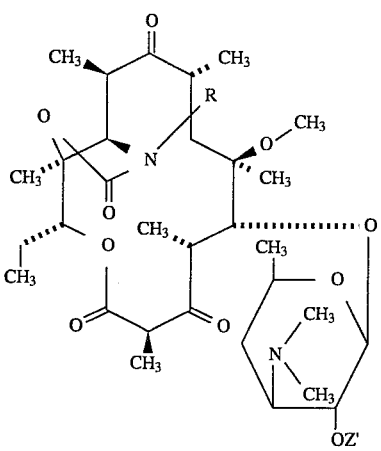

corresponding to the product of formula I in which Z is other than hydrogen, or to the action of carbonyldiimidazole to obtain a compound of the formula

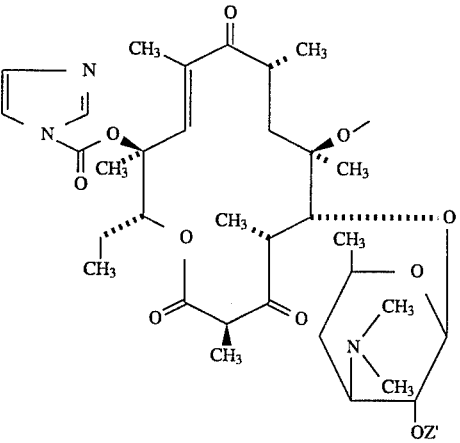

then to the action of a compound of the formula $$RNH_2 \quad VIII$$

wherein R has the above definition to obtain the compound of formula VI which is cyclized spontaneously by heating or which is subjected to the action of a cyclization agent to obtain the corresponding compound of formula IA, then if appropriate the compound of formula IA is subjected to the action of an agent which releases the 2' hydroxyl and/or if appropriate, to the action of an acid to form the salt.

In a preferred mode of the process of the invention, the agent capable of selectively activating the 11-hydroxyl is a sulfonic anhydride such as methane sulfonic, p-toluene sulfonic or trifluoromethane sulfonic anhydride, and the base capable of creating a 10(11) double bond is a diazabicycloundecene, for example DBU (or 1,8-diazabicyclo-[5-4-0]-undec-7-ene), or diazabicyclononene, or 2,6-lutidine, or 2,4,6-collidine or tetramethylguanidine. The reaction between the compound of formula IV and the compound of formula V takes place in the presence of a base such as pyridine, triethyl-amine, morpholine, N-methyl morpholine and cyclization of the compound of formula VI is achieved either spontaneously or by heating at a temperature between 50° and 100°.

The reaction of the compound of formula IV with carbonyldiimidazole take place in the presence of a base such as sodium hydride, triethylamine, or sodium or potassium carbonate or bicarbonate, or in the absence of a base in a solvent such as methylene chloride, tetrahydrofuran or dimethylformamide. The reaction of the compound of formula VII with $RNH_2$ takes place in a solvent such as acetonitrile, dimethylformamide or tetrahydrofuran, dimethoxy ethane or dimethylsulfoxide and the cyclization of the compound of formula VI takes place during the reaction or is achieved by the action of a base such as potassium terbutylate on the isolated compound of formula VI in a solvent such as tetrahydrofuran. Hydrolysis of the 2'-ester function is carried out using methanol or aqueous hydrochloric acid and salification is carried out using acids by standard processes.

The compounds of formula II are products which are known generally and can be prepared as indicated in the European Patent Application No. 0,487,411. The compounds of formulae $RN=C=O$ and $RNH_2$ are also generally known and the latter compounds can be described by the process of Ann. Chem., Vol. 690, pgs 98–114.

The antibiotic compositions of the invention are comprised of an antibiotically effective amount of a compound of formula I or its non-toxic, pharmaceutically acceptable acid addition salt and an inert pharmaceutical carrier. The compositions may be in the form of tablets, dragees, capsules, granules, suppositories, ointments, creams, gels or injectable solutions or suspensions or a powder to be dissolved just before use in a pyrogenic sterile water, for example.

Examples of suitable excipients or carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions possess a very good antibiotic activity on gram+bacteria such as staphylococci, streptococci, pneumococci and are useful in the treatment of infections caused by sensitive germs and particularly, in that of staphylococcia, such as staphylococcal septicemias, malignant staphylococcia of the face or skin, pyodermatitis, septic or suppurating sores, boils, anthrax, phlegmons, erysipelas and acne, staphylococcia such as acute primary or post-influenzal anginas, bronchopneumonia, pulmonary suppuration, streptococcia such as acute anginas, otitis, sinusitis, scarlet fever, pneumococcia such as pneumonia, bronchitis; brucellosis, diphtheria, gonococcal infection.

The compositions are also active against infections caused by germs such as Hemophilus influenzae, Rickettsiaes, Mycoplasma pneumoniaes, Chlamydia, Legionella, Ureaplasma, Toxoplasma, or by germs of the Mycobacterium, Listeria, Meningococcal and Campylobacter type.

The novel method of the invention for treating bacterial infections in warm-blooded animals comprises administering to warm-blooded animals an antibactericidally effective amount of a compound of formula I or its acid addition salt. The compounds may be administered orally, rectally, parenterally or topically to the skin or macous membrane, preferably orally. The usual daily doses is 0.66 to 4.0 mg/kg depending on the condition treated, the specific compound and the method of administration.

In the following examples, there are described several preferred embodiments to illustrate the invention. However, it is to be understood that the invention is not intended to be limited to the specific embodiments.

EXAMPLE 1

11,12-Dideoxy-3-de(2,6-dideoxy-3-C-methyl-3-0-methyl-α-L-ribohexopyranosyl-oxy)-6-0-methyl-3-oxo-12,11-(oxycarbonyl-[(4-phenyl-3-butenyl)imino)] erythromycin

STAGE A 3-de((2,6-Dideoxy-3-C-methyl-3-0-methyl-α-L-ribohexopyranosyl)oxy)-6-0-methyl-11-0-(methylsulfonyl)-3-oxo-erythromycin-2'-acetate 17 g of 3-de[(2,6-dideoxy-3-C-methyl-3-0-methyl-α-L-ribohexopyranosyl)-oxy]-6-0-methyl-3-oxo-erythromycin-2'-acetate were introduced with stirring under a nitrogen atmosphere into 100 ml of pyridine and the mixture was cooled to 10° C. 11.9 g of methane sulfonic anhydride were added and the mixture was allowed to return to ambient temperature. The mixture was stirred for 5 hours and the precipitate was filtered off. After concentrating, taking up in water and extracting with ethyl acetate, the organic phases were washed with water, dried, filtered and concentrated to obtain 20.9 g of crude product which was purified by salification with oxalic acid, then release of the base with ammonium hydroxide to obtain 15.16 g of the desired product melting at 210°–212° C.

STAGE B

11-Deoxy-10,11-didehydro-3-de(2,6-dideoxy-3-C-methyl-3-0-methyl-α-L-ribohexopyranosyl)oxy)-6-0-methyl-3-oxo-erythromycin-2'-acetate 8.26 g of the product of Stage A were introduced with stirring into 35 ml of acetone and 2.19 ml of DBU were then added dropwise. The mixture was stirred at ambient temperature for 20 hours and then was taken up in methylene chloride. The organic phases were washed with water, dried over sodium sulfate, filtered and concentrated to obtain 10 g of product which was taken up in ether. Separation was carried out, followed by washing with ethyl ether to obtain 6.33 g of the desired product melting at 230°–232° C.

STAGE C

11-Deoxy-10,11-didehydro-3-de(2,6-dideoxy-3-C-methyl-3-0-methyl-α-L-ribohexopyranosyl-oxy)-12-0-[(1H-imidazol-1-yl)-carbonyl]-6-0-methyl-3-oxo-erythromycin-2'-acetate 96 mg of sodium hydride at 50% in oil were introduced into 15 ml of tetrahydrofuran and the suspension was cooled to 0° C. A solution of 611 mg of the product of Stage B in 17 ml of tetrahydrofuran was introduced dropwise and then a solution of 486 mg of carbonyldiimidazole in 15 ml of tetrahydrofuran was introduced at 0° C. The mixture was stirred for 4 hours 30 minutes and was then allowed to return to ambient temperature, filtered and concentrated. The residue was taken up in ethyl acetate, washed with sodium dihydrogen phosphate and extraction was carried out with ethyl acetate. The extracts were dried, filtered and concentrated to obtain 852 mg of the desired product.

STAGE D 11,12-Deoxy-3-de[2,6-dideoxy-3-C-methyl-3-0-methyl-α-L-ribohexopyranosyl-oxy]-6-0-methyl-3-oxo-12,11-(oxycarbonyl-[(4-phenyl-3-butenyl)-imino]-erythromycin-2'-acetate A mixture of 0.9 g of 11-deoxy-10,11-didehydro-3-de[((2,6-dideoxy-3-C-methyl-3-0-methyl-α-L-ribohexopyranosyl)-oxy)]-12-0-[(1H-imidazol-1-yl)-carbonyl]-6-0-methyl- 3-oxo-erythromycin-2'-acetate, 3 ml of acetonitrile and 0.6 g of 4-phenyl-3-butenylamine was stirred for 5 hours 30 minutes at 55° C. and was then poured into a 0.5M aqueous solution of sodium dihydrogen phosphate. Extraction was carried out with ethyl acetate and the extracts were washed with water, dried, filtered and concentrated to obtain 0.9 g of an oil which was chromatographed on silica, eluting with an ethyl acetate-triethylamine mixture (96-4). The homogeneous phases were collected by thin layer chromatography and concentrated to obtain 0.32 g of a product which was impasted in hexane, separated and dried at 70° C. to obtain 0.215 g of the desired product melting at 201°–203° C.

STAGE E 11,12-Dideoxy-3-de[((2,6-dideoxy-3-C-methyl-3-0-methyl-α-L-ribohexopyranosyl)-oxy)]-6-0-methyl-3-oxo-12,11-(oxycarbonyl-[(4-phenyl-3-butenyl)-imino)-erythromycin A solution of 0.194 g of the product of Stage A and 6 ml of methanol was stirred at ambient temperature for 15 hours and then the methanol was evaporated off in a rotary evaporator. The product was chromatographed on silica, eluting with a methylene chloride-methanol-ammonium hydroxide mixture (95-5-0.2) and the homogeneous phases were collected, concentrated, dried, filtered and concentrated to obtain 0.155 g of product which was separated and dried at 70° C. to obtain 0.124 g of the desired product melting at 257°–259° C.

Using the procedure of Example 1 and the appropriate amines, the following products were prepared:

EXAMPLE 2

(Z)11,12-Dideoxy-3-de((2,6-dideoxy-3-C-methyl-3-0-methyl-α-L-ribohexopyranosyl)-oxy)-6-0-methyl-3-oxo-12,11-(oxycarbonyl-[(4-(4-fluorophenyl-3-butenyl)-imino]-erythromycin melting at 222° C.

EXAMPLE 3

(Z)11,12-Dideoxy-3-de[(2,6-dideoxy-3-C-methyl-3-0-methyl-α-L-ribohexopyranosyl)-oxy]-6-0-methyl-3-oxo-12,11-(oxycarbonyl-[4-(4-trifluoromethyl-3-butenyl)-imino]-erythromycin melting at 230° C.

EXAMPLE 4

(cis)11,12-Dideoxy-3-de[(2,6-dideoxy-3-C-methyl-3-0-methyl-α-L-ribohexopyranosyl)-oxy]-6-0-methyl-3-oxo-12,11-(oxycarbonyl-[(4-phenyl-3-butenyl)-imino)]-erythromycin melting at 220°–225° C. and having a specific rotation of $[\alpha]_D=+10.5°$ (c=0.9% is $CHCl_3$)

EXAMPLE 5

(E)11,12-Dideoxy-3-de[(2,6-dideoxy-3-C-methyl-3-0-methyl-α-L-ribohexopyranosyl)-oxy]-6-0-methyl-3-oxo-12,11-(oxycarbonyl-[(4-phenyl-2-butenyl)-imino)]-erythromycin melting at approximately 78° C.

EXAMPLE 6

(Z)11,12-Dideoxy-3-de[(2,6-dideoxy-3-C-methyl-3-0-methyl-α-L-ribohexopyranosyl)-oxy]-6-0-methyl-3-oxo-12,11-(oxycarbonyl-[(4-phenyl-3-butenyl)-imino]-erythromycin melting at 220° C. and having a specific rotation of $[\alpha]_D=+16°$ (C=1% in $CHCl_3$)

EXAMPLE 7

11,12-Dideoxy-3-de[(2,6-dideoxy-3-C-methyl-3-0-methyl-α-L-ribohexopyranosyl)-oxy]-6-0-methyl-3-oxo-12,11-(oxycarbonyl-[(4-phenyl-3-butynyl)-imino])-erythromycin melting at 252° C.

EXAMPLE 8

11,12-Dideoxy-3-de[(2,6-dideoxy-3-C-methyl-3-0-methyl-α-L-ribohexopyranosyl)-oxy]-6-0-methyl-3-oxo-12,11-(oxycarbonyl-[(4-phenyl-2-butynyl)-imino])-erythromycin melting at approximately 98° C.

EXAMPLE 9

(E)11,12-Dideoxy-3-de[(2,6-dideoxy-3-C-methyl-3-0-methyl-α-L-ribohexopyranosyl)-oxy]-6-0-methyl-3-oxo-12,11-(oxycarbonyl-[(4-(1,2'-biphenyl-4-yl)-3-butenyl)-imino])]-erythromycin melting at 215°–217° C. and having a specific rotation of $[\alpha]_D=-46.5°$ (C=1% in $CHCl_3$)

EXAMPLE 10

(Z)11,12-Dideoxy-3-de[(2,6-dideoxy-3-C-methyl-3-0-methyl-α-L-ribohexopyranosyl)-oxy]-6-0-methyl-3-oxo-12,11-(oxycarbonyl-[(4-(1,2'-biphenyl-4-yl)-3-butenyl]-imino)-erythromycin melting at 133°–137° C. and having a specific rotation of $[\alpha]_D=-2.5°$ (c=1% in $CHCl_3$)

Operating in an identical manner, the following products were prepared

| Z | R |
|---|---|
| H | 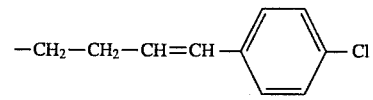 |

| Z | R |
|---|---|
| H | 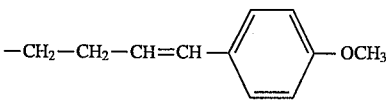 |

PREPARATION 1

[4-Fluorophenyl-4-yl]-3-butenylamine

STAGE A

N-[[4-Fluorophenyl-4-yl]-3-butenyl]-phthalamide

A suspension of 150 ml of tetrahydrofuran, 6 g of 4-fluorobenzaldehyde and 25.6 g of N-(3-bromopropyl)-phthalamide triphenyl phosphonium bromide was cooled to −40° C. and 5.42 g of potassium terbutylate were added. The temperature was allowed to rise to −15° C. and the mixture was stirred for one hour. The mixture was poured over ice and extraction was carried out with ethyl acetate. The organic phases were washed with water, dried over $Na_2SO_4$, filtered and concentrated to obtain 26.7 g of product which was dissolved in methylene chloride and chromatography on silica was carried out, eluting with an ethyl acetate - hexane mixture (1-9). The residue was concentrated under reduced pressure to obtain 5.2 g of the desired product melting at 94° C.

| ANALYSIS: | | | |
|---|---|---|---|
| | % calculated | | % found |
| C % | 73.40 | C % | 73.2 |
| H % | 4.77 | H % | 4.8 |
| N % | 4.74 | N % | 4.6 |
| F % | 4.43 | F % | 6.6 |

STAGE B

[4-Fluorophenyl-4-yl]-3-butenylamine

A mixture of 200 ml of ethanol, 5.5 g of the product of Stage A, and 1.5 ml of hydrazine hydrate was stirred for 16 hours at 0° C. and the mixture was allowed to return to ambient temperature. The solvent was evaporated off and the residue was taken up in ether, followed by acidification to pH=1 using a 2N hydrochloric acid solution. The solvent was eliminated and the residue was taken up in water. A sodium carbonate solution was added and extraction was carried out with ether and the solvents were evaporated off. After chromatography of the residue on silica (eluant: methylene chloride-methanol-ammonium hydroxide 9-1-0.5), 2.2 g of the expected product were obtained.

PREPARATION 2

[4-Trifluoromethyl-phenyl-4-yl]-3-butenyl-amine

STAGE A

N-[(4-Trifluoromethyl-4-yl)-3-butenyl]-phthalamide

Using the procedure of Stage A of Preparation 1, 6 g of 4-(trifluoromethyl)-benzaldehyde were reacted to obtain 4 g of the expected product melting at 88° C.

STAGE B

[4-Trifluoromethyl-phenyl-4-yl]-3-butenylamine

Using the procedure of Stage B of Preparation 1, 2.13 g of the product of Stage A and 0.84 ml of hydrazine hydrate were reacted to obtain 0.850 g of the expected amine.

PREPARATION 3

4-[(1,1'-Biphenyl)-4-yl]-3-butenylamine

STAGE A

N-[4[(1,1'-Biphenyl-4-yl]-3-butenyl]-phthalimide

A suspension of 150 ml of tetrahydrofuran, 5.46 g of 4-phenylbenzaldehyde and 15.9 g of N-(3-bromopropyl)-phthalimide triphenyl phosphonium bromide was cooled to −40° C. and 3.37 g of potassium terbutylate was then introduced. The temperature was allowed to rise to −15° C. and the mixture was stirred at −15° C. for one hour. The mixture was poured over ice and extraction was carried out with ethyl acetate. The extracts were washed with water and the organic phases were dried over $Na_2SO_4$, filtered and concentrated to obtain 19 g of product which was dissolved in methylene chloride. Chromatography on silica was carried out, eluting with an ethyl acetate - hexane mixture (3-7) and the residue was concentrated, impasted in hexane, followed by separation and drying under reduced pressure to obtain 8.5 g of the desired product melting at approximately 112°–114° C.

| ANALYSIS: | | | |
|---|---|---|---|
| | % calculated | | % found |
| C % | 81.56 | C % | 81.4 |
| H % | 5.42 | H % | 5.3 |
| N % | 3.96 | N % | 3.8 |

STAGE B

4-[(1,1'-Biphenyl)-4-yl]-3-butenylamine

A mixture of 280 ml of ethanol, 7.9 g of the product of Stage A and 1.3 ml of hydrazine hydrate was refluxed and then allowed to return to ambient temperature. The precipitate was filtered off and washed with ethanol. After concentration, the product was poured into a 2N hydrochloric acid solution and extraction was carried out with ethyl acetate. The organic phase was washed with water, dried, filtered and concentrated under reduced pressure to obtain 2.89 g of the desired product melting at approximately 188°–194° C.

EXAMPLE OF PHARMACEUTICAL COMPOSITION

Tablets were prepared containing 150 mg of the product of Example 1 and sufficient excipient of starch, talc and magnesium stearate for a 1 g tablet.

PHARMACOLOGICAL STUDY

Method of Dilutions in Liquid Medium

A series of tubes was prepared into which an equal quantity of sterile nutritive medium was divided and increasing quantities of the product to be studied were distributed into each tube. Then, each tube was seeded with a bacterial strain and after incubation for 24 hours in a heating chamber at 37° C., the growth inhibition was evaluated by transillumination which allowed the minimal inhibiting concentrations (M.I.C), expressed in micrograms/ml to be determined.

The following results were obtained with the product of Example 1: (reading after 24 hours)

| GRAM+ bacterial strains | M.I.C. of mg |
|---|---|
| *Staphylococcus aureus* 011UC4 | 0.04 |
| *Staphylococcus aureus* 011HT17 | 0.04 |
| *Staphylococcus aureus* 011G025I | 0.08 |
| *Staphylococcus epidermidis* 012G011C | 0.08 |
| *Streptococcus pyogenes* Group A 02A1UC1 | ≦0.02 |
| *Streptococcus agalactiae* Group B 02B1HT1 | 0.08 |
| *Streptococcus sp* Group C 02COCB3 | ≦0.02 |
| *Streptococcus faecalis* Group D 02D2UC1 | 0.04 |
| *Streptococcus faecium* Group D 02D3HT1 | ≦0.02 |
| *Streptococcus sp* Group G 02GOGR5 | <0.02 |
| *Streptococcus mitis* 02mitCB1 | ≦0.02 |
| *Streptococcus agalactiae* Group B 02B1SJ1 | 0.3 |
| *Streptococcus sp* Group C 02COCB1 | 0.15 |
| *Streptococcus pneumoniae* 032UC1 | 0.08 |
| *Streptococcus pnuemoniae* 030SJ1 | 2.5 |
| *Streptococcus pneumoniae* 030SJ5 | 0.08 |

Furthermore, the product of Example 1 displayed a useful activity on the GRAM⊖ bacterial strains Haemophilus Influenza 351HT3, 351CB12, 351CA1 and 351GR6.

Various modifications of the compositions and method of the invention may be made without departing from the spirit or scope thereof and it is to be understood that the invention is intended to be limited only as defined in the appended claims.

What is claimed is:

1. A compound of the formula

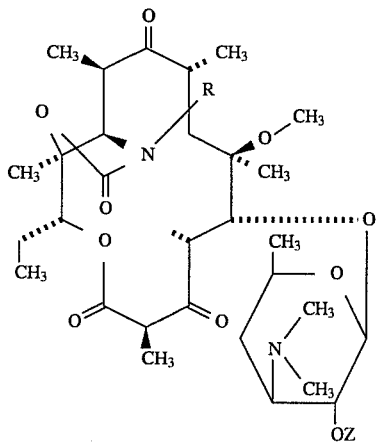

wherein R is

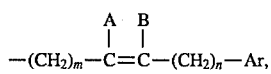

m and n are individually integers from 0 to 6, A and B are individually a member selected from the group consisting of hydrogen, halogen and alkyl of 1 to 8 carbon atoms, the double bond geometry being E or Z or E+Z or A and B form a third bond between the carbon atoms to which they are attached, Ar is selected from the group consisting of a) phenyl and naphthyl optionally substituted with a member of the group consisting of —CF$_3$, phenyl, free carboxy, alkoxycarbonyl, carboxy salified with a non-toxic, pharmaceutically acceptable base, amidified carboxy, —OH, halogen, —NO$_2$, —CN, alkyl, alkenyl, alkynyl, alkoxy, alkenyloxy, alkynyloxy, alkylthio, alkenylthio and alkynylthio of up to 12 carbon atoms, N-alkyl, N-alkenyl and N-alkynyl of up to 12 carbon atoms, cycloalkyl of 3 to 12 carbon atoms and

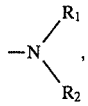

all aliphatic groups optionally substituted with at least one halogen, R$_1$ and R$_2$ are individually selected from the group consisting of hydrogen, alkyl of 1 to 12 carbon atoms, phenyl, naphthyl, phenoxy, naphthyloxy, phenylthio, naphthylthio, thienyl, furyl, pyrrolyl, thiazolyl, pyridyl, pyrimidinyl, pyridazinyl, pyrazinyl, indolyl, benzofuryl, benythienyl and quinolinyl, all optionally substituted as above and b) heterocyclic aryl selected from the group consisting of thienyl, furyl, pyrrolyl, thiazolyl, pyridyl, pyrimidinyl, pyridazinyl, pyrazinyl, indolyl, benzofuryl, benythienyl and quinolinyl, Z is hydrogen or acyl of an organic carboxylic acid of 1 to 18 carbon atoms, or its non-toxic, pharmaceutically acceptable acid addition salt.

2. A compound of claim 1 wherein Z is hydrogen.
3. A compound of claim 1 wherein A and B are hydrogen.
4. A compound of claim 1 wherein A and B form a third bond.
5. A compound of claim 1 wherein m is 1 or 2.
6. A compound of claim 1 wherein n is 0 or 1.
7. A compound of claim 1 wherein Ar is phenyl optionally substituted with fluorine, —CF$_3$ or phenyl.
8. A compound of claim 1 wherein Ar is phenyl.
9. A compound of claim 1 wherein the compound is 11,12-dideoxy-3-de[(2,6-dideoxy-3-C-methyl-3-0-methyl-α-L-ribohexopyranosyl)oxy]-6-0-methyl-3-oxo-12,11-

(oxycarbonyl-[(4-phenyl-3-butenyl)-imino]-erythromycin and its non-toxic, pharmaceutically acceptable acid addition salts.

10. A compound of claim 1 wherein Ar is phenyl or naphthyl, both optionally substituted with a member of the group consisting of free carboxy, alkoxycarbonyl, carboxy salified with a non-toxic, pharmaceutically acceptable base, amidified carboxy, —OH, halogen, —NO$_2$, —CN, alkyl, alkenyl, alkynyl, alkoxy, alkenyloxy, alkynyloxy, alkylthio, alkenylthio and alkynylthio of up to 12 carbon atoms, N-alkyl, N-alkenyl and N-alkynyl of up to 12 carbon atoms, cycloalkyl of 3 to 12 carbon atoms and,

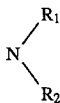

all aliphatic groups optionally substituted with at least one halogen, R$_1$ and R$_2$ are individually selected from the group consisting of hydrogen, alkyl of 1 to 12 carbon atoms phenyl naphthyl, phenoxy, naphthyloxy, phenylthio, naphthylthio and thienyl.

11. An antibiotic composition comprising an antibiotically effective amount of a compound of claim 1 and an inert pharmaceutical carrier.

12. A composition of claim 11 wherein the compound is 11,12-dideoxy-3-de[(2,6-dideoxy-3-C-methyl-3-0-methyl-α-L-ribohexopyranosyl)oxy]-6-0-methyl-3-oxo-12,11-(oxycarbonyl-[(4-phenyl-3-butenyl)-imino]-erythromycin and its non-toxic, pharmaceutically acceptable acid addition salts.

13. A method of combatting bacterial infections in warm-blooded animals comprising administering to said warm-blooded animals an antibiotically effective amount of a compound of claim 1.

14. A method of claim 13 wherein Z is hydrogen.

15. A method of claim 13 wherein A and B are hydrogen.

16. A method of claim 13 wherein A and B form a third bond.

17. A method of claim 13 wherein m is 1 or 2.

18. A method of claim 13 wherein n is 0 or 1.

19. A method of claim 13 wherein Ar is phenyl optionally substituted with fluorine, —CF$_3$ or phenyl.

20. A method of claim 13 wherein Ar is phenyl.

21. The method of claim 13 wherein the compound is 11,12-dideoxy-3-de[(2,6-dideoxy-3-C-methyl-3-0-methyl-α-L-ribohexopyranosyl)oxy]-6-0-methyl-3-oxo-12,11-(oxycarbonyl-[(4-phenyl-3-butenyl)-imino]-erythromycin and its non-toxic, pharmaceutically acceptable acid addition.

22. A method of claim 13 wherein Ar is phenyl or naphthyl, both optionally substituted with a member of the group consisting of free carboxy, alkoxycarbonyl, carboxy salified with a non-toxic, pharmaceutically acceptable base, amidified carboxy, —OH, halogen, —NO$_2$, —CN, alkyl, alkenyl, alkynyl, alkoxy, alkenyloxy, alkenyloxy, alkylthio, alkenylthio and alkynylthio of up to 12 carbon atoms, N-alkyl, N-alkenyl and N-alkynyl of up to 12 carbon atoms, cylcloalkyl of 3 to 12 carbon atoms and R$_1$

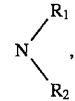

all aliphatic groups optionally substituted with at least one halogen, R$_1$ and R$_2$ are individually selected from the group consisting of hydrogen, alkyl of 1 to 12 carbon atoms, phenyl, naphthyl, phenoxy, naphthyloxy, phenylthio, naphthylthio and thienyl.

* * * * *